(12) United States Patent
Manzer et al.

(10) Patent No.: US 6,706,935 B2
(45) Date of Patent: Mar. 16, 2004

(54) CATALYTIC EQUILIBRATION TO INCREASE THE RELATIVE MOLE FRACTION OF $CF_3CHCl$, $CF_3CHCl_2$ OR $CF_3CF_2H$ IN A COMPOSITION

(75) Inventors: Leo Ernest Manzer, Wilmington, DE (US); Frank Julian Weigert, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/359,357

(22) Filed: Feb. 6, 2003

(65) Prior Publication Data

US 2003/0139634 A1 Jul. 24, 2003

Related U.S. Application Data

(63) Continuation of application No. 07/974,197, filed on Nov. 10, 1992, now abandoned, which is a continuation of application No. 07/560,516, filed on Jul. 31, 1990, now abandoned.

(51) Int. Cl.[7] .................... C07C 17/00; C07C 19/08; C07C 21/18; C07C 23/00; C07C 25/13; C07C 17/08
(52) U.S. Cl. ............................... 570/163; 570/169
(58) Field of Search ............................. 570/163, 169

(56) References Cited

U.S. PATENT DOCUMENTS

| | | | |
|---|---|---|---|
| 2,478,932 A | 8/1949 | Miller et al. |
| 2,687,441 A | 8/1954 | Price et al. |
| 3,258,500 A | 6/1966 | Swamer et al. |
| 3,651,156 A | 3/1972 | Scherer et al. |
| 3,787,331 A | 1/1974 | Groppelli et al. |
| 3,793,229 A | 2/1974 | Groppelli et al. |
| 4,069,266 A | 1/1978 | Komatsu et al. |
| 4,145,368 A | 3/1979 | Sweeney et al. |
| 4,158,675 A | 6/1979 | Potter |
| 4,605,798 A | 8/1986 | Abel et al. |
| 4,766,260 A | 8/1988 | Manzer et al. |
| 5,008,476 A | 4/1991 | Manzer et al. |
| 5,030,372 A | 7/1991 | Manogue et al. |
| 5,345,014 A | 9/1994 | Cuzzato |

FOREIGN PATENT DOCUMENTS

| | | |
|---|---|---|
| EP | 0365296 | 10/1989 |
| GB | 873212 | 7/1961 |
| GB | 2030981 | 4/1980 |
| JP | 5527138 | 2/1980 |
| WO | WO92/19576 | 11/1992 |

OTHER PUBLICATIONS

Chem. Abst. 113:23097c Jul. 16, 1990 (relates to Japanese Kokai Tokkyo Koho JP 0 240,332).

*Primary Examiner*—Johann Richter
*Assistant Examiner*—Elvis O. Price

(57) ABSTRACT

A method is disclosed for increasing in a composition the mole fraction of a compound selected from the group $CF_3CHCl_2$, $CF_3CHF_2$ and $CF_3CHClF$ relative to the total mole fraction of the other two compounds of the group. The method comprises (a) providing a gaseous composition comprising at least one compound of said group provided that (i) if the selected compound is either $CF_3CHCl_2$ or $CF_3CHF_2$, said gaseous composition comprises $CF_3CHFCl$ and the mole fraction of the selected compound relative to the other two compounds in said gaseous composition is less than its equilibrium amount at 50° C., and (ii) if the selected compound is $CF_3CHFCl$, said gaseous composition comprises both $CF_3CHCl_2$ and $CF_3CHF_2$ and the mole fraction of the selected compound relative to the other two compounds in said gaseous composition is less than its equilibrium amount at 500° C.; (b) contacting said gaseous composition with a catalyst selected from the group of catalysts consisting of catalysts comprising chromium as an oxide, as a halide or as a halided oxide, in a valence state of three to six, and supported catalysts containing at least one metal selected from cobalt, copper, iron, manganese, nickel and zinc for a time sufficient to provide substantial equilibrium between the three compounds having said formula; and (c) providing during said catalyst contact a temperature within the range of about 50° C. to 500° C. at which the mole fraction of the selected compound relative to the other two compounds increases.

20 Claims, No Drawings

CATALYTIC EQUILIBRATION TO INCREASE THE RELATIVE MOLE FRACTION OF CF₃CHCl, CF₃CHCl₂ OR CF₃CF₂H IN A COMPOSITION

This application is a continuation of application Ser. No. 07/974,197 filed Nov. 10, 1992, now abandoned, which is a continuation of application Ser. No. 07/560,516 filed Jul. 31, 1990, now abandoned.

FIELD OF THE INVENTION

This invention relates to the preparation of halogen substituted hydrocarbons and more particularly to the use of equilibrium reactions for preparing halogen substituted hydrocarbons containing fluorine.

BACKGROUND OF THE INVENTION

There has been considerable recent interest in halogen substituted ethanes containing fluorine and hydrogen. Many of these materials can be used not only as blowing agents and refrigerants, but also as starting materials for preparing other useful compounds.

U.S. Pat. No. 4,766,260 discloses an improved gas-phase process for the manufacture of 1,1,1-trifluorodichloroethane (i.e., HCFC-123) and 1,1,1,2-tetrafluorochloroethane (i.e., HCFC-124) by contacting a suitable tetrahaloethylene with hydrogen fluoride in the presence of a selected metal on a high fluorine content alumina support, the reaction being conducted under controlled conditions whereby the production of pentafluoroethane (i.e., HFC-125) is minimized. U.S. Pat. No. 4,766,260 discloses that intermediates formed during the course of the invention, such as $CHF_2CClF_2$, $CHClFCClF_2$, $CHCl_2CClF_2$, $CClF=CCl_2$ and $CHCl_2CCl_2F$ can be recycled to the reactor for the production of additional 1,1,1-trifluorodichloroethane and 1,1,1,2-tetrafluorochloroethane; and that 1,1,1-trifluorodichloroethane can be recycled to the reactor for the production of additional 1,1,1,2-tetrafluorochloroethane when this is desired. It is often desirable to avoid the use and production of unsaturated materials, and there is thus a need for additional techniques which selectively yield saturated halogen substituted hydrocarbons containing fluorine and hydrogen such as HCFC-123, HCFC-124 and HFC-125.

Chromium-containing catalysts have been used in conjunction with disproportionations and other reactions involving halogen-substituted ethanes. For example, U.S. Pat. No. 4,145,368 discloses a process for manufacturing 1,1,1-trifluoro-2,2-dichloroethane by reaction of 1,1,1-trifluoro-2,2,2-trichloroethane with 1,1,1-trifluoro-2-chloroethane over a solid catalyst such as $Cr_2O_3$. The use of catalysts containing chromium in a valence state of three to six and either oxide alone or oxide and fluoride is disclosed. U.S. Pat. No. 3,787,331 discloses use of a chromium-containing catalyst in disproportionating and isomerizing $CF_2Cl—CFCl_2$; and U.S. Pat. No. 3,651,156 exemplifies the disproportionation reaction of $C_2F_3Cl_3$ passed over a catalyst obtained by fluorination of chromium hydroxide.

U.S. Pat. No. 4,605,798 discloses a process for the preparation of trichlorotrifluoroethanes, dichlorotetrafluoroethanes, and monochloropentafluoroethane utilizing three reactors, one of which is used for a fluorination-dismutation reaction. The catalysts used in these reactors comprise supported or non-supported oxides or halides of chromium among others.

SUMMARY OF THE INVENTION

We have found that catalysts selected from the group of catalysts consisting of catalysts containing chromium in a valence state of three to six as an oxide, a halide, or as halided oxide and supported catalysts containing at least one metal selected from cobalt, copper, iron, manganese, nickel and zinc are effective in equilibrating $CF_3CFHCl$ with its disproportionation products $CF_3CHCl_2$ and $CF_3CF_2H$; and that the equilibration constant for the disproportionation varies with temperature over the range of 50° C. to 500° C., with the formation of $CF_3CFHCl$ becoming more favored as the temperature increases.

The present invention involves at least partial equilibration of the halohydrocarbon $CF_3CFHCl$ (HCFC-124) with halohydrocarbons $CF_3CHCl_2$ (HCFC-123) and $CF_3CF_2H$ (HFC-125) using a vapor phase reaction. In this equilibration the halogens on the carbon containing the hydrogen exchange. All the compounds involved in the interconversion contain exactly two carbons and one hydrogen.

A method is provided in accordance with this invention for increasing in a composition the mole fraction of a selected compound of the formula $CF_3CHF_xCl_{2-x}$ where x is an integer from 0 to 2 relative to the total mole fraction of the other two compounds having said formula which comprises the steps of: (a) providing a gaseous composition comprising at least one compound of said formula provided that (i) if the selected compound is either $CF_3CHCl_2$ or $CF_3CHF_2$, said gaseous composition comprises $CF_3CHFCl$ and the mole fraction of the selected compound relative to the other two compounds in said gaseous composition is less than its equilibrium amount at 50° C., and (ii) if the selected compound is $CF_3CHFCl$, said gaseous composition comprises $CF_3CHCl_2$ and $CF_3CHF_2$ and the mole fraction of the selected compound relative to the other two compounds in said gaseous composition is less than its equilibrium amount at 500° C.; (b) contacting said gaseous composition with a catalyst selected from the group of catalysts consisting of catalysts comprising chromium as an oxide, as a halide or as a halided oxide, in a valence state of three to six, and supported catalysts containing at least one metal selected from cobalt, copper, iron, manganese, nickel and zinc, for a time sufficient to provide substantial interconversion among the three compounds having said formula; and (c) providing during said catalyst contact a temperature within the range of about 50° C. to 500° C. at which the mole fraction of the selected compound relative to the other two compounds increases.

The method, preferably supplemented by the steps of separating at least a portion of the selected compound from the interconverted composition of step (c); and contacting at least a portion of the compounds remaining after said separation with a catalyst selected from said group of catalysts at a temperature within the range of about 50° C. to 500° C. and for a time sufficient to produce an additional quantity of said selected compound by providing substantial interconversion; can be advantageously included in a process for preparing halogen substituted ethanes to increase the yield of the selected compound relative to the total yield of the other two compounds having the above-referenced formula.

DETAILS OF THE INVENTION

The invention deals with processes employing the interconversion of $CF_3CFHCl$ (HCFC-124) with $CF_3CHCl_2$ (HCFC-123) and $CF_3CF_2H$ (HCFC-125) using selected catalysts. The preferred catalysts of this invention comprise chromium in a valence state of three to six as an oxide (e.g., $Cr_2O_3$), as a halide (e.g., $CrX_3$ where each X is selected from chlorine and fluorine) or as a halided oxide (e.g., $Cr_2O_3$ treated with $CCl_3F$ or $CCl_4$). The chromium catalysts of this invention can be supported or unsupported. Other catalysts which may be used for the interconversion of this invention include supported catalysts containing at least one metal selected from cobalt, copper, iron, manganese, nickel and zinc.

A method is provided in accordance with this invention for increasing in a composition the mole fraction of a selected compound of the formula $CF_3CHF_xCl_{2-x}$ where x is an integer from 0 to 2 relative to the total mole fraction of the other two compounds having said formula comprising the steps of: (a) providing a gaseous composition comprising at least one compound of said formula provided that (i) if the selected compound is either $CF_3CHCl_2$ or $CF_3CHF_2$, said gaseous composition comprises $CF_3CHFCl$ and the mole fraction of the selected compound relative to the other two compounds in said gaseous composition is less than its equilibrium amount at 50° C., and (ii) if the selected compound is $CF_3CHFCl$, said gaseous composition comprises both $CF_3CHCl_2$ and $CF_3CHF_2$ and the mole fraction of the selected compound relative to the other two compounds in said gaseous composition is less than its equilibrium amount at 500° C.; (b) contacting said gaseous composition, with a catalyst selected from the group of catalysts consisting of catalysts comprising chromium as an oxide, as a halide or as a halided oxide, in a valence state of three to six, and supported catalysts containing at least one metal selected from cobalt, copper, iron, manganese, nickel and zinc, for a time sufficient to provide substantial interconversion among the three compounds having said formula; and (c) providing during said catalyst contact a temperature within the range of about 50° C. to 500° C. at which the mole fraction of the selected compound relative to the other two compounds increases.

Suitable compositions comprising the compounds of the formula $CF_3CHF_xCl_{2-x}$ may be provided as a product (e.g., a reaction product) containing all three compounds. Alternatively either HCFC-124, or both HCFC-123 and HFC-125 may be provided. It will be evident that even where HCFC-124 is initially provided without HCFC-123 and/or HFC-125 or where both HCFC-123 and HFC-125 are initially provided without HCFC-124, even partial equilibration will produce a quantity of the compound(s) not initially provided. Accordingly, gaseous mixtures comprising all three compounds of the formula $CF_3CHF_xCl_{2-x}$ may be provided in accordance with step (a), and interconversion (i.e., disproportionation or conproportionation) among HCFC-124, HCFC-123, and HFC-125 may be achieved in accordance with this invention at suitable temperatures.

The chromium catalysts of this invention can be used as a single component or combined with a support such as alumina or carbon. The catalysts of this invention which do not contain chromium (i.e., catalysts containing cobalt, copper, iron, manganese, nickel and/or zinc) should be supported. Supported catalysts (e.g., supported chromium oxides) can be prepared by impregnation of a pre-formed support, co-precipitation or co-evaporation. Such methods are well-known in the art. Reference is made to U.S. Pat. No. 4,766,260 for further discussion of supported metal catalysts.

The preferred catalysts of this invention contain chromium as an oxide, as a halide, or as a halided oxide. By halided chromium oxide is meant a material comprising chromium, oxygen, and a halogen, the halogen being either chlorine or fluorine. The halogen content can vary from 1% to nearly 10% with either halogen. The remainder of the material may include chromium oxide.

Catalysts based on fluorided chromia ($Cr_2O_3$) can be prepared prior to reaction by treatment with a vaporizable fluorine-containing fluorinating compound, such as HF, $CCl_3F$ (CFC-11), $CClF_2$ (CFC-12), or $CCl_2FCClF_2$ (CFC-113). Catalysts based on chlorided chromia can be prepared prior to reaction by treatment with a vaporizable chlorine-containing chlorinating compound, such as $CCl_4$ or $C_2Cl_4$. The surface halogenation takes place at elevated temperatures until the desired degree of fluorination is obtained, e.g., at about 200° C. to about 450° C. The treatment can conveniently be done in the reactor which is to be used for equilibration.

A suitable catalyst may be prepared, for example, as follows:

A quantity of chromia ($Cr_2O_3$) is dried until essentially all moisture is removed, e.g., for about 2 hours at 400° C. The dried catalyst is then transferred to the reactor to be used. The temperature is then lowered to about 200° C., and CFC-12 in $N_2$ is passed through the reactor. The $N_2$ can be gradually reduced until only CFC-12 is being passed through the reactor. At this point the temperature is increased to about 350° C. and held at that temperature to convert the $Cr_2O_3$ to the desired halide content. If too much activator is used, the resulting bulk $CrX_3$ will not be as active as surface treated oxide. If too little is used, further activation will occur when the actual process is started.

The interconversion using the catalyst of the instant invention is conducted at 50° C. to 500° C., preferably about 200° C. to 400° C. Depending upon the selected compound desired, mixtures of HCFC-124, HCFC-123 and HFC-125 in any proportion may be used as feed to the equilibration reactor. Preferably, where it is desirable to produce $CF_3CFHCl$, the gaseous composition of step (a) is derived from a feed of $CF_3CHCl_2$ and $CF_3CHF_2$; and where it is desirable to produce $CF_3CHCl_2$ and/or $CF_3CHF_2$, the gaseous composition of step (a) is derived from a feed of $CF_3CFHCl$.

The contact time in the vapor phase process can vary widely depending on the degree of conversion desired and generally will be about 5 to 180 seconds, preferably about 60 to 90 seconds.

The halohydrocarbon may be fed as is or diluted with an inert gas such as nitrogen, helium or argon.

The interconversion of HCFC-124 with HCFC-123 and HFC-125 may be conducted in any suitable reactor, including fixed and fluidized bed reactors. The reaction vessel should be constructed from materials which are resistant to the corrosive effects of hydrogen halides, such as Hastelloy® nickel alloy and Inconel® nickel alloy.

In accordance with this invention a method is provided for increasing the yield of a selected compound of the formula $CF_3CHF_xCl_{2-x}$ where x is an integer from 0 to 2 relative to the total yield of the other two compounds having said formula in a process for preparing halogen substituted ethanes containing fluorine. A preferred method includes the steps of (a) providing a gaseous composition comprising at least one compound of said formula provided that (i) if the selected compound is either $CF_3CHCl_2$ or $CF_3CHF_2$, said gaseous composition comprises $CF_3CHFCl$ and the mole fraction of the selected compound relative to the other two compounds in said gaseous composition is less than its equilibrium amount at 50° C., and (ii) if the selected compound is $CF_3CHFCl$, said gaseous composition comprises both $CF_3CHF_2$ and $CF_3CHCl_2$ and the mole fraction of the selected compound relative to the other two compounds in said gaseous composition is less than its equilibrium amount at 500° C.; (b) contacting said gaseous composition with a catalyst selected from the group of catalysts consisting of catalysts comprising chromium as an oxide, as a halide or as a halided oxide, in a valence state of three to six, and supported catalysts containing at least one metal selected from cobalt, copper, iron, manganese, nickel and zinc, for a time sufficient to provide substantial interconversion among the three compounds having said formula; and (c) providing during said catalyst contact a temperature within the range of about 50° C. to 500° C. at which the mole fraction of the selected compound relative to the other two compounds increases; (d) separating at least a portion of the selected compound from the interconverted composition of step (c); and (e) contacting at least a portion of the compounds remaining after said separation with a catalyst selected from the group of catalysts consisting of catalysts comprising chromium as an oxide, as a halide or as a halided oxide in a valence state of three to six, and supported catalysts containing at least one metal selected from cobalt, iron, manganese, nickel, and zinc, at a temperature within the range of about 50° C. to 500° C. and for a time sufficient to produce an additional quantity of said selected compound by providing substantial interconversion.

Pressure is not critical. Atmospheric and superatmospheric pressures are the most convenient and are therefore preferred.

Separation of the selected compound as provided by step (d) may be accomplished by conventional methods (e.g., fractional distillation). The catalyst contact step (e) can be accomplished in a separate contact unit or can, where suitable, be accomplished by recycling of compounds remaining after separation to the catalyst contact of steps (b) and (c).

HFC-125 and HCFC-123 may be used in accordance with this invention to provide HCFC-124 which is an important reagent for producing the refrigerant $CF_3CH_2F$. This invention allows HFC-125 produced during commercial HCFC-124 production by hydrofluorination to be recycled with intermediate HCFC-123 for added HCFC-124 production. The interconversion can also produce HFC-125 from HCFC-124 without requiring equipment resistant to HF. The product fluorocarbons of this invention are useful as refrigerants.

Practice of the invention will be made further apparent from the following non-limiting examples.

EXAMPLES

In illustrative Examples 1 through 6 which follow, all parts and percentages are by weight and all temperatures are Celsius. All product compositions are relative area based on gas chromatographic analyses, and are uncorrected for relative response.

General Procedure for Equilibration in Examples 1 through 6

The temperature was adjusted to the indicated values, followed by the initiation of flow of the halohydrocarbon(s). All flows were adjusted to give the feed rates and contact times indicated in the Examples. The reactor effluent was sampled on line by a Varian-6000 gas chromatograph using a 10 foot×⅛" ID column containing Krytox® perfluorinated polyether on an inert support and a helium flow of 20–35 cc/minute. Gas chromatographic conditions were 70° C. for 6.5 min. followed by temperature programming to 180° C. at a rate of 35° C./min. A flame ionization detector was used to provide relative areas.

Example 1

This Example uses a $Cr_2O_3$ catalyst to disproportionate HCFC-124. The results at various temperatures are shown in Table 1.

Catalyst: 5 g $Cr_2O_3$, no pretreatment
Feed: HCFC-124 (5 mL/min)

TABLE 1

| Temp | K (app)* |
|---|---|
| start: | 0.0 |
| 120° C. | $3.2 \times 10^3$ |
| 140° C. | $3.1 \times 10^2$ |
| 175° C. | 19 |
| 218° C. | 4.5 |
| 238° C. | 1.1 |
| 256° C. | 1.0 |
| 258° C. | 0.71 |
| 277° C. | 0.30 |
| 307° C. | 0.28 |

$$*K(app) = \frac{(\text{relative area HFC-125})(\text{relative area HCFC-123})}{(\text{relative area HCFC-124})^2}$$

It is evident from the results above that the formation of HFC-125 and HCFC-123 are favored at lower temperatures.

Example 2

This Example demonstrates the conproportionation reaction whereby HCFC-124 is made from HCFC-123 and HFC-125. The results are shown in Table 2.

Catalyst: 10 g $Cr_2O_3$ no pretreatment
Flows: HCFC-123 liquid @ 2 mL/hr and HFC-125 gas ~5 cc/min

TABLE 2

| Temp | F125[1] | F124a[m] | F124[n] | F123a[p] | F123[q] |
|---|---|---|---|---|---|
| 277° C. | 71.5 | 0.29 | 41.4 | 1.9 | 266 |

[1]F125 = $CF_3CHF_2$ (HFC-125)
[m]F124a = $CHF_2CClF_2$ (HCFC-124a)
[n]F124 = $CF_3CHClF$ (HCFC-124)
[p]F123a = $CHF_2CCl_2F$ (HCFC-123a)
[q]F123 = $CF_3CHCl_2$ (HCFC-123)

It is evident that HCFC-123 and HFC-125 were substantially interconverted to HFC-124.

Example 3

This Example demonstrates disproportionation at various temperatures using supported $Cr_2O_3$ catalyst. The results are shown in Table 3.

Catalyst: 4 g 7.5% $Cr_2O_3/Al_2O_3$
Activation: 15 min @ 300° C. with $CCl_4$ at 2 mL/h
Feed: HCFC-124 (with 0.4% HCFC-124a) at 10 mL/min

TABLE 3

| Temp | F125 | F124a | F124 | F123 |
|---|---|---|---|---|
| 50° C. | 0.13 | 0.03 | 45 | 5 |
| 76° C. | 1.10 | 0.03 | 39 | 11 |
| 160° C. | 5.8 | — | 12 | 32 |

Example 4

This Example demonstrates disproportionation at various temperatures using supported $Cr_2O_3$ catalyst. The results are shown in Table 4.

Catalyst: 7.3 g 19% $Cr_2O_3/Al_2O_3$
Activation: 300° C. with CFC-12 @ 25 mL/min for 30 min
Feed: HCFC-124, 5 mL/min

TABLE 4

| Temp | F124a | F124 | F125 | F123a | F123 |
|---|---|---|---|---|---|
| 187° C. | 0.18 | 28 | 4.3 | 0.07 | 8.3 |
| 191° C. | 0.21 | 34 | 2.1 | <.01 | 5.4 |
| 294° C. | 0.30 | 27 | 3.8 | 0.03 | 8.1 |
| 346° C. | 0.36 | 22 | 1.5 | 0.05 | 7.5 |

It is evident from Examples 3 and 4 that the interconversion of HCFC-124 to HFC-125 and HCFC-123 proceeds in the presence of supported $Cr_2O_3$.

Example 5

This Example demonstrates the conproportionation reaction whereby HCFC-124 can be made from HCFC-123 and a mixture of materials containing HFC-125. The results are shown in Table 5.

Catalyst: 10 g $Cr_2O_3$ (Pretreat: 30 min 385° C. 6 mL/h $CCl_4$)
Flows: Liquid, 1 mL/hr; gas, 15 cc/min

TABLE 5

| Temp | F116[q] | F125 | F115[r] | F124 | F114a[s] | F123 |
|---|---|---|---|---|---|---|
| start gas | 3.4 | 11.5 | 78 | none | 7.3 | none |
| start liquid | | | | | | 100 |
| 297° C. | 2.8 | 17.4 | 140 | 5.0 | 1.1 | 8.7 |
| 355° C. | 2.4 | 12.8 | 120 | 5.6 | 0.9 | 11.4 |
| 400° C. | 2.2 | 11.4 | 120 | 5.1 | 1.0 | 9.7 |
| 450° C. | 2.3 | 12.5 | 120 | 4.5 | 3.9 | 8.2 |

[q] $F116 = CF_3CF_3$ (FC-116)
[r] $F115 = CF_3CClF_2$ (CFC-115)
[s] $F114a = CF_3CCl_2F$ (CFC-114a)

It is evident that the interconversions of this invention can be achieved in the presence of various other halogen substituted hydrocarbons.

Example 6

This Example demonstrates the effect of temperature on the equilibrium. Low temperature favors disproportionation. High temperature favors conproportionation. The results at various temperatures is shown in Table 6.

Catalyst: 30 g $Cr_2O_3$
Activation: 350–375° C. with CFC-12 @ ~20/min.
Feed: F124 ~5 mL/min

TABLE 6

| Temp | F125 | F115 | F124a | F124 | F133a | F114a | F123 | K (app) |
|---|---|---|---|---|---|---|---|---|
| 200° C. | 88 | 7 | 0.3 | 33 | 24 | 4.5 | 128 | 10.0 |
| 249° C. | 52 | 36 | 0.4 | 19.6 | 64 | 4.3 | 56 | 7.6 |
| 298° C. | 18 | 48 | 0.4 | 9.6 | 30 | 3.9 | 24 | 4.7 |
| 347° C. | 13 | 41 | 0.9 | 7.5 | 12.5 | 5.5 | 15.4 | 3.6 |
| 400° C. | 9 | 32 | 0.8 | 4.8 | 3.4 | 3.9 | 8.3 | 3.2 |

It is evident that at the relatively large catalyst dosage of this example, various other by-products can be produced in addition to the interconversion products of this invention, especially at high temperatures.

Example 7

$CF_3CHClF \rightarrow CF_3CHCl_2 + CF_3CHF_2$

A 0.5" ID×12" long Inconel® nickel alloy pipe was charged with 23.1 g (30 mL) of 29% $CrCl_3$/carbon. The bath was gradually heated to 400° C. while nitrogen gas at a flow rate of 50 mL/min was passed through the reactor to remove traces of water. The temperature was then decreased to 350° C. and nitrogen/HCFC-124 (6/1 molar ratio) was passed over the catalyst at a contact time of 30 s. The reactor effluent was analyzed with a Hewlett Packard HP 5890 gas chromatograph using a 20 foot long, ⅛" diameter, column containing Krytox® perfluorinated polyether on an inert support and a helium flow of 35 cc/min. Gas chromatographic conditions were 70° C. for 3 minutes followed by temperature programming to 180° C. at a rate of 6° C./min. The results of the reaction are shown in Table 7.

TABLE 7

| F125 | F124 | F114a[t] | F123 | PCE[u] | Others |
|---|---|---|---|---|---|
| 32.4% | 19.6% | 4.7% | 34.5% | 3.2% | 5.6% |

[t] $F114a = CF_3CCl_2F$ (CFC-114a)
[u] $PCE = CCl_2=CCl_2$

It is evident that interconversion of HCFC-124 to HFC-125 and HCFC-123 proceeds in the presence of supported $CrCl_3$ catalyst.

Example 8

HCFC-124 Disproportionation

A 0.5" ID×12" long Inconel® nickel alloy pipe was charged with 2% $CoCl_2/Al_2O_3$ (20.4 g, 30 mL). The bath was gradually heated to 176° C. while nitrogen gas at a flow rate of 50 cc/min was passed through the reactor to remove traces of water. The $H_2$/HF flow was continued at a bath temperature of 176° C. for four hours. The HF flow was then stopped and only $N_2$ was passed over the catalyst overnight at a 176° C. The HF flow was started again the next day. After 10 minutes the HF flow was increased to 75 cc/min and the $N_2$ flow decreased to 25 cc/min. The bath temperature was then increased to 263° C. at the higher HF flow rate and maintained under those conditions for 1.3 hours followed by the following heating profile: 281° C./13 min;

313° C./22 min; 352° C./15 min; and finally at 399° C. for 15 min. The HF flow was then stopped and the temperature of the bath reduced to reaction temperature. The results of passing HCFC-124 over the activated catalyst at a contact time of 60 seconds except for the experiment at 350° C. for which the contact time was 30 seconds is shown in the table. The reactor effluent was analyzed with a Hewlett Packard HP 5890 gas chromatograph using a 20 foot long, 1/8" diameter, column containing Krytox® perfluorinated polyether on an inert support and a helium flow of 35 cc/min. Gas chromatographic conditions were 70° C. for 3 minutes followed by temperature programming to 180° C. at a rate of 6° C./min. The results of the reaction are shown in Table 8.

TABLE 8

| Temp. | $N_2$/F-124 | % F125 | % F124 | % F123 | % Others |
|---|---|---|---|---|---|
| start | 1/1 | 0.2 | 99 | 0.1 | 0.2 |
| 125° C. | 0/1 | 2 | 96 | 2 | 0.7 |
| 150° C. | 0/1 | 4 | 91 | 4 | 0.4 |
| 250° C. | 0/1 | 24 | 51 | 24 | 0.6 |
| 350° C. | 1/1 | 38 | 30 | 22 | 10* |

*Included in others for this run was 0.6% $CF_3CClF_2$, 3% $CCl_2=CClF$, 1.6% $CClF_2CCl_3$ and 3.6% $CCl_2=CCl_2$.

It is evident that interconversion of HCFC-124 to HFC-125 and HCFC-123 proceeds in the presence of supported $CoCl_2$ catalyst.

Particular embodiments of the invention are included in the Examples. Other embodiments of the invention will become apparent to those skilled in the art from a consideration of the specification or practice of the invention disclosed herein. It is understood that modifications and variations may be practiced without departing from the spirit and scope of the novel concepts of this invention. It is further understood that the invention is not confined to the particular formulations and examples herein illustrated, but it embraces such modified forms thereof as come within the scope of the claims.

What is claimed is:

1. A process for preparing pentafluoroethane, which consists essentially of contacting a $CF_3CHClF$ feed in the gas phase with a catalyst consisting of chrome oxide ($Cr_2O_3$) at temperatures ranging from 175° C. to 307° C.

2. In a process for preparing pentafluoroethane, a step which consists essentially of:

interconverting $CF_3CHClF$ with $CF_3CHCl_2$ and pentafluoroethane in the gas phase by contacting $CF_3CHClF$ with a catalyst at a temperature within the range of about 50° C. to 500° C. to provide a product comprising pentafluoroethane, provided that the mole fraction of any pentafluoroethane in the gas contacted with said catalyst, prior to said catalyst contact, is less than its equilibrium amount relative to $CF_3CHClF$ and $CF_3CHCl_2$ at the catalyst contact temperature, and that the $CF_3$ CHClF is contacted with a catalyst selected from the group consisting of (i) catalysts comprising chromium as an oxide, as a halide or as a halided oxide, in the valence state of three to six and (ii) supported catalysts containing at least one metal selected from cobalt, copper, iron, manganese, nickel and zinc.

3. The process of claim 2 wherein the catalyst comprises $Cr_2O_3$.

4. The process of claim 2 wherein the catalyst comprises a halided oxide of chromium.

5. The process of claim 4 wherein the catalyst consists essentially of $Cr_2O_3$ on alumina which has been fluorided.

6. The process of claim 2 wherein the catalyst consist essentially of supported or unsupported $Cr_2O_3$.

7. The process of claim 2 wherein the catalyst is selected from the group consisting of $Cr_2O_3$ supported on alumina, $CrCl_3$ supported on carbon and $CoCl_2$ supported on $Al_2O_3$.

8. The process of claim 2 wherein the catalyst contact temperature is within the range of about 120° C. to 307° C.

9. A process for preparing pentafluoropentane, comprising:

providing a product comprising pentafluoropentane using the process of claim 2;
   separating at least a portion of the pentafluoroethane from said product; and, optionally,
   contacting at least a portion of the compounds remaining after said separation with a catalyst from said group at a temperature within the range of about 50° C. to 500° C. to increase the yield of pentafluoroethane relative to $CF_3CHClF$ and $CF_3CHCl_2$.

10. A method for increasing the mole fraction of pentafluoroethane in a composition relative to the total mole fraction of $CF_3CHClF$ and $CF_3CHCl_2$ therein, comprising the steps of:

(a) providing a gaseous composition consisting essentially of halogen substituted hydrocarbons comprising $CF_3CHClF$ wherein the mole fraction of pentafluoroethane relative to $CF_3CHClF$ and $CF_3CHCl_2$ is less than its equilibrium amount at 50° C.;

(b) contacting said gaseous composition with a catalyst selected from the group consisting of (i) catalysts comprising chromium as an oxide, as a halide or as a halided oxide, in the valence state of three to six and (ii) supported catalysts containing at least one metal selected from cobalt, copper, iron, manganese, nickel and zinc, for a time sufficient to provide substantial interconversion among pentafluoroethane, $CF_3CHClF$ and $CF_3CHCl_2$; and (c) providing during said catalyst contact a temperature within the range of about 50° C. to 500° C. at which the mole fraction of pentafluoroethane increases relative to the total mole fraction of $CF_3CHClF$ and $CF_3CHCl_2$.

11. The method of claim 10 wherein the catalyst comprises $Cr_2O_3$.

12. The method of claim 11 wherein the catalyst consists essentially of alumina-supported $Cr_2O_3$ which has been fluorided.

13. The method of claim 11 wherein the catalyst contact temperature is within the range of about 120° C. to 307° C.

14. In a process for preparing $CF_3CHCl_2$, a step which consists essentially of:

interconverting $CF_3CHClF$ with $CF_3CHCl_2$ and $CF_3CHF_2$ in the gas phase by contacting $CF_3CHClF$ with a catalyst at a temperature within the range of about 50° C. to 500° C. to provide a product comprising $CF_3CHCl_2$, provided that the mole fraction of any $CF_3CHCl_2$ in the gas contacted with said catalyst, prior to said catalyst contact, is less than its equilibrium amount relative to $CF_3CHClF$ and $CF_3CHF_2$ at the catalyst contact temperature, and that the $CF_3CHClF$ is contacted with a catalyst selected from the group consisting of catalysts comprising $Cr_2O_3$.

15. The process of claim 14 wherein the catalyst consists essentially of $Cr_2O_3$ on alumina which has been fluorided.

16. The process of claim 14 wherein the catalyst contact temperature is within the range of about 120° C. to 307° C.

17. A method for increasing the mole fraction of $CF_3CHCl_2$ in a composition relative to the total mole fraction of $CF_3CHClF$ and $CF_3CHF_2$ therein, comprising the steps of:

(d) providing a gaseous composition consisting essentially of halogen substituted hydrocarbons comprising $CF_3CHClF$ wherein the mole fraction of $CF_3CHCl_2$ relative to $CF_3CHClF$ and $CF_3CHF_2$ is less than its equilibrium amount at 50° C.;

(e) contacting said gaseous composition with a catalyst selected from the group consisting of (i) catalysts comprising chromium as an oxide, as a halide or as a halided oxide, in the valence state of three to six and (ii) supported catalysts containing at least one metal selected from cobalt, copper, iron, manganese, nickel and zinc, for a time sufficient to provide substantial interconversion among $CF_3CHF_2$, $CF_3CHClF$ and $CF_3CHCl_2$; and (f) providing during said catalyst contact a temperature within the range of about 50° C. to 500° C. at which the mole fraction of $CF_3CHCl_2$ increases relative to the total mole fraction of $CF_3CHClF$ and $CF_3CHF_2$.

18. The method of claim 17 wherein the catalyst comprises supported $Cr_2O_3$.

19. The method of claim 17 wherein the catalyst consists essentially of unsupported or alumina-supported $Cr_2O_3$ which has been fluorided.

20. The method of claim 17 wherein the catalyst contact temperature is within the range of about 120° C. to 307° C.

* * * * *